United States Patent
Han et al.

(10) Patent No.: US 11,124,784 B2
(45) Date of Patent: Sep. 21, 2021

(54) **CHITINOLYTIC ENZYME DERIVED FROM *CLOSTRIDIUM CELLULOVORANS***

(71) Applicant: Korea University Research and Business Foundation, Seoul (KR)

(72) Inventors: Sung Ok Han, Seoul (KR); Myeong Eun Lee, Sejong-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/922,324

(22) Filed: Jul. 7, 2020

(65) Prior Publication Data
US 2021/0009976 A1 Jan. 14, 2021

(30) Foreign Application Priority Data

Jul. 9, 2019 (KR) .................. 10-2019-0082666
Jan. 15, 2020 (KR) .................. 10-2020-0005288

(51) Int. Cl.
| | | |
|---|---|---|
| *C12N 1/21* | (2006.01) | |
| *C12N 9/24* | (2006.01) | |
| *C12P 19/14* | (2006.01) | |
| *C12N 15/56* | (2006.01) | |
| *C12N 9/42* | (2006.01) | |
| *C12N 15/70* | (2006.01) | |

(52) U.S. Cl.
CPC .......... *C12N 9/2442* (2013.01); *C12N 15/70* (2013.01); *C12P 19/14* (2013.01); *C12Y 302/01014* (2013.01)

(58) Field of Classification Search
None
See application file for complete search history.

(56) References Cited

FOREIGN PATENT DOCUMENTS

| | | | |
|---|---|---|---|
| KR | 10-0628416 B1 | 9/2006 | |
| KR | 10-2009-0085379 A | 8/2009 | |
| KR | 10-2011-0117556 A | 10/2011 | |
| WO | WO-2010101158 A1 * | 9/2010 | ..... C12Y 302/01055 |
| WO | WO-2012111810 A1 * | 8/2012 | .............. C12P 19/26 |

OTHER PUBLICATIONS

Guo et al., Protein tolerance to random amino acid change, Proc. Natl. Acad. Sci. USA 101, 2004, 9205-10. (Year: 2004).*
Uniprot, Accession No. D9SUC4, 2019, www.uniprot.org. (Year: 2019).*
Qing et al., Cold-shock induced high-yield protein production in *Escherichia coli*, Nature Biotechnol. 22, 2004, 877-82. (Year: 2004).*
Nishihara et al., Overexpression of trigger factor prevents aggregation of recombinant proteins in *Escherichia coli*, Appl. Environ. Microbiol. 66, 2000, 884-89. (Year: 2000).*
Kim et al., The Unique Role of Novel Cellulosomal Subunit in *Clostridium cellulovorans* Explored by Cohesin Marker Related to Binding on Insoluble Cellulosic Substrate, Korean Society of Biological Engineering Conference 2015, abstract, 2015, p. 349. (Year: 2015).*
Xing Fu et al., "An acidic, thermostable exochitinase with ß-N-acetylglucosaminidase activity from Paenibacillus barengoltzii converting chitin to N-acetyl glucosamine", Biotechnology for Biofuels, 2014, pp. 1-11, vol. 7, No. 174.
Myeong-Eun Lee et al., "Identification and Applications of a Novel Chitinolysis Supporting Protein (CSP) from Enzyme Components of Cellulosome in *Clostridium cellulovorans*", The Korean Society for Biotechnology and Bioengineering, Oct. 2018, 2 pgs.; http://www.dbpia.co.kr/journal/articleDetail?nodeId=NODE07558115.
Myeong-Eun Lee et al., "Identification and Application of a Novel Chitinolysis Supporting Exo-glycosidase (CSE) from Enzyme Components of Cellulosome in Clostridium cellulovorans", Biotechnology from the Nature to Human Life, Apr. 10-12, 2019, 3 pgs.
Communication dated Dec. 21, 2020, issued by the Korean Intellectual Property Office in application No. 10-2020-0005288.
GenBank: BAV13043.1, hypothetical protein [*Clostridium cellulovorans*], Jun. 1, 2016 (2 pages).
Communication dated Jan. 27, 2021, issued by the Korean Intellectual Property Office in application No. 10-2020-0005288.
Reguera et al., "Chitin degradation by cellulolytic anaerobes and facultative areobes from soils and sediments", FEMS Microbiology Letters, 2001, vol. 204, pp. 367-374 (8 pages).

* cited by examiner

*Primary Examiner* — Robert B Mondesi
*Assistant Examiner* — Todd M Epstein
(74) *Attorney, Agent, or Firm* — Sughrue Mion, PLLC

(57) ABSTRACT

The present disclosure relates to a novel chitinolytic enzyme, particularly to a chitinolytic enzyme including an exo-β-N-acetylglucosaminidase (Clocel_3193) constituting a cellulosome derived from *Clostridium cellulovorans* as an active ingredient. The present disclosure allows utilization of chitin biomass which has not been used formerly as a raw material and allows environment-friendly production of N-acetylglucosamine. In addition, since the Clocel_3193 has a cell wall binding ability and degrading ability, the Clocel_3193 may be used in an antifungal composition.

5 Claims, 4 Drawing Sheets

Specification includes a Sequence Listing.

[FIG. 1]
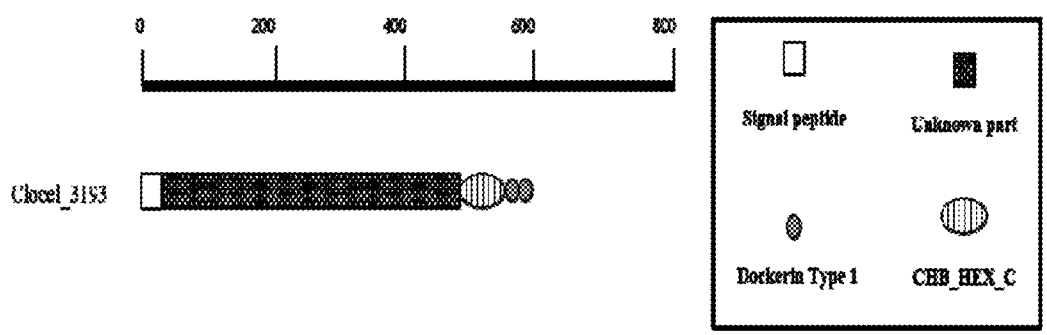
[FIG. 2]
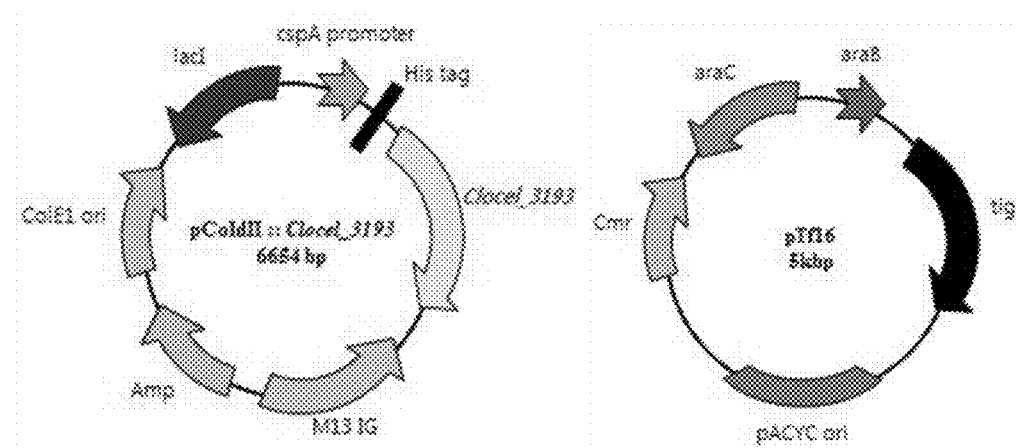

[FIG. 3]
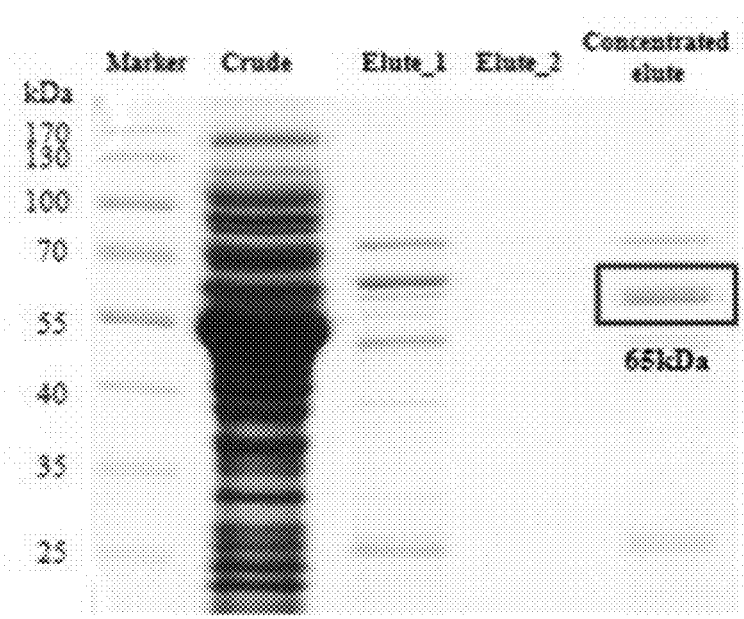
[FIG. 4]
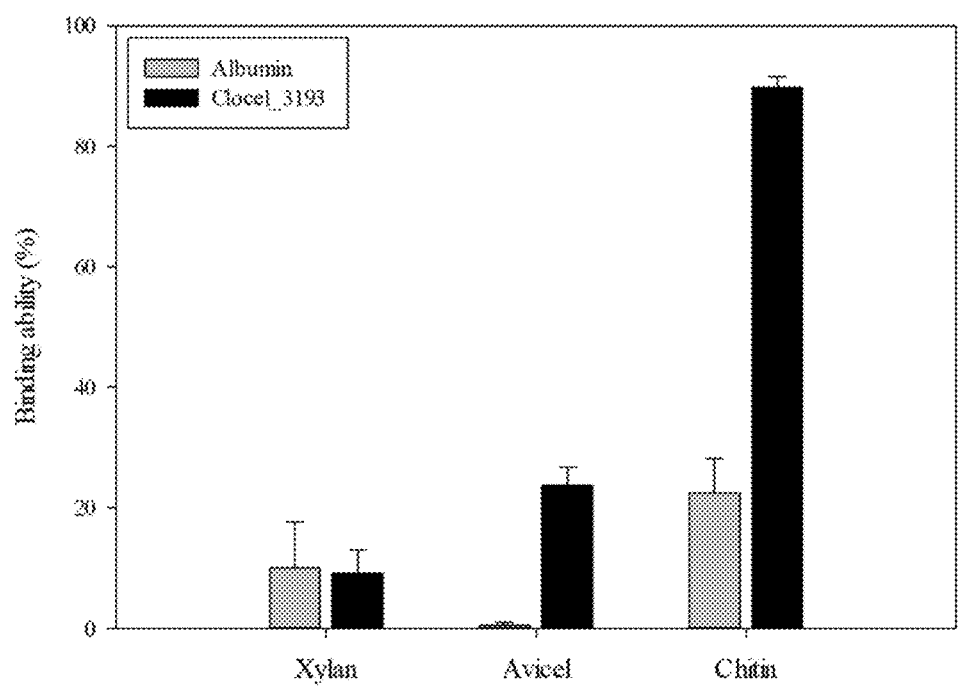

[FIG. 5]
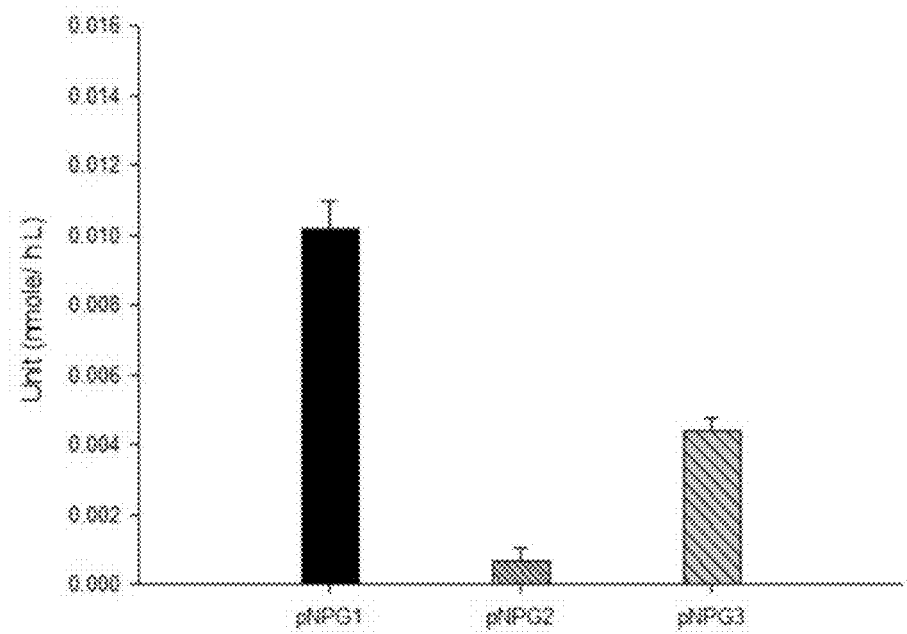
[FIG. 6]
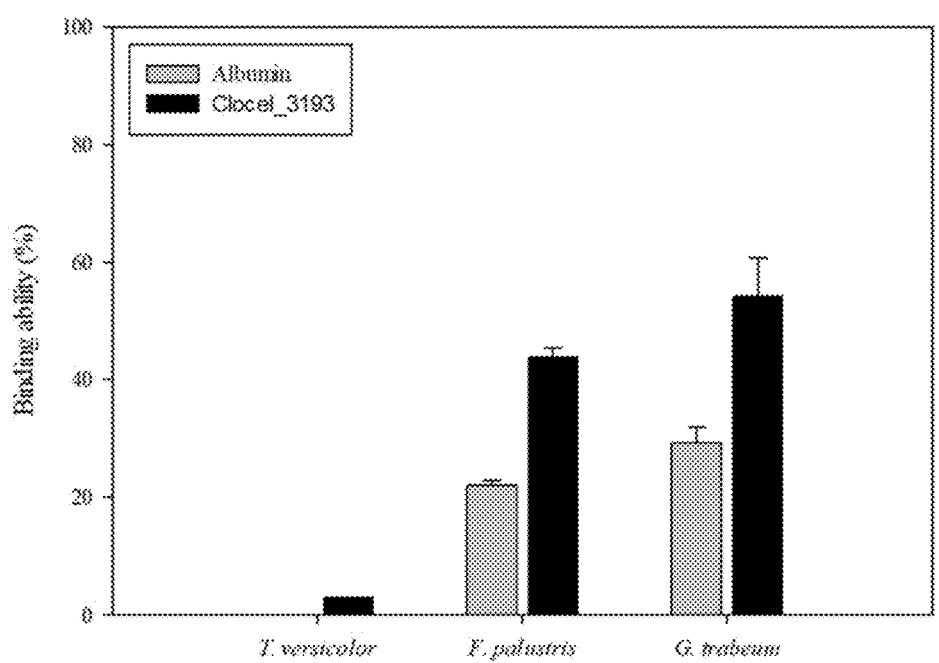

[FIG. 7]
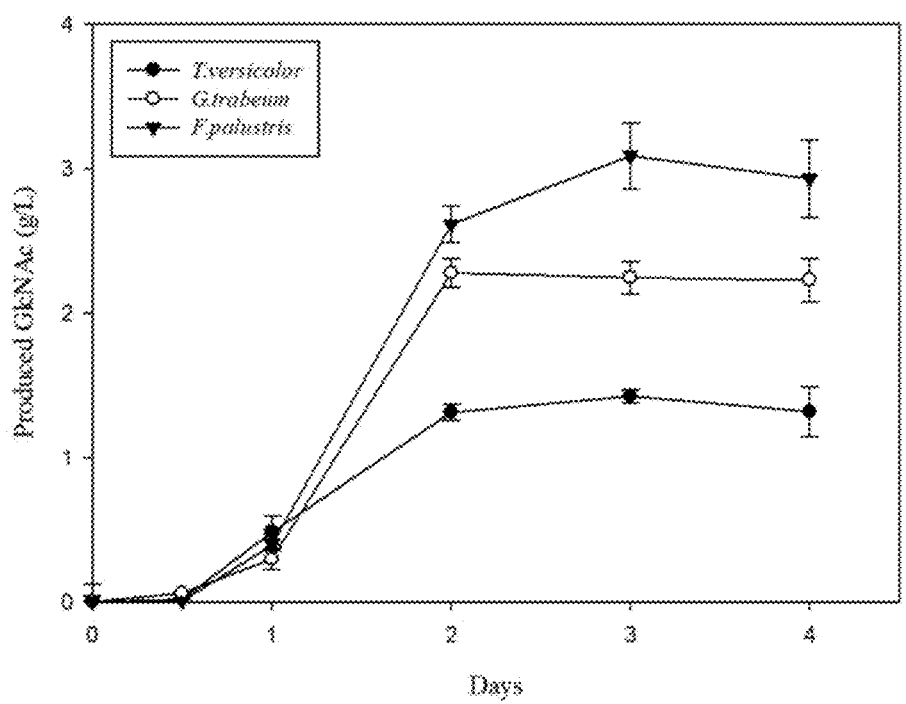

CHITINOLYTIC ENZYME DERIVED FROM *CLOSTRIDIUM CELLULOVORANS*

SEQUENCE LISTING

The content of the electronically submitted sequence listing, file name: Sequencelistingasfiled.txt; size: 7657 bytes; and date of creation: Jun. 10, 2020, filed herewith, is incorporated herein by reference in its entirety.

TECHNICAL FIELD

The present disclosure relates to a novel chitinolytic enzyme, particularly to a chitinolytic enzyme including an exo-β-N-acetylglucosaminidase constituting a cellulosome derived from *Clostridium cellulovorans* as an active ingredient.

BACKGROUND ART

In general, biomass-degrading anaerobic microorganisms have enzyme complexes called cellulosomes on the cell wall. They express various enzymes depending on the substrates available from outside, bind to the cell wall, and effectively acquire nutrients utilizing various enzymes.

The various enzymes attached to the cellulosomes are associated with lignocellulosic biomass such as cellulose, xylan, mannan and pectin from which carbon sources can be obtained. Unlike the carbon sources, only a few enzymes of the cellulosomes are known from which nitrogen sources can be obtained. The representative examples are chitinolytic enzymes.

Although nitrogen sources are nonexistent in lignocellulosic biomass, nitrogen sources are required in addition to carbon sources for normal growth of *Clostridium*. At present, it is presumed that the microorganisms acquire N-acetylglucosamine, which is an amine-attached sugar, by degrading molds, yeast or dead insects that may be present in the lignocellulosic biomass and utilize it as a nitrogen source. Among the enzymes that constitute the cellulosome of *Clostridium cellulovorans*, an enzyme associated with a nitrogen source has not been found yet.

In general, a chitinolytic enzyme produces the N-acetylglucosamine sugar by degrading the polysaccharide chitin present in the exoskeletons of insects and crustaceans. Chitobiase is known as a chitinolytic enzyme which recognizes and cleaves two N-acetylglucosamine units. In addition, β-hexosaminidase, which is an enzyme that cleaves hexose, is also a chitinolytic enzyme. Exo-β-N-acetylglucosaminidase (GlcNAcase), which is a member of the family of hexosaminidases, is also a chitinolytic enzyme.

Exo-β-N-acetylglucosaminidase (GlcNAcase) is a chitinolytic enzyme which recognizes and cleaves the terminal N-acetylglucosamine of a non-reducing sugar one by one.

N-Acetylglucosamine, which is an amino sugar formed from an amino acid and a sugar, is known as an essential component of cartilage. It is a functional sugar industrially useful as a dietary adjuvant helpful for inflammatory and ulcerous bowel diseases and arthritis, for bioethanol production through fermentation of sugar, as a moisturizing substance of functional cosmetic products, etc.

Meanwhile, chitin accounts for 22-44% of the cell wall of molds. Therefore, an enzyme having chitin degrading activity may be utilized for production of industrially useful N-acetylglucosamine or as an anti-mold agent.

REFERENCES OF RELATED ART

Non-Patent Documents

Fu et al. *Biotechnology for Biofuels* 2014, 7:174.

DISCLOSURE

Technical Problem

The present disclosure is directed to providing a novel chitinolytic enzyme derived from *Clostridium cellulovorans*.

The present disclosure is also directed to providing a method for preparing the chitinolytic enzyme and an antifungal composition containing the chitinolytic enzyme as an active ingredient.

However, the technical problems to be solved by the present disclosure are not limited to those described above and other problems not mentioned above will be clearly understood by those of ordinary skill in the art from the following description.

Technical Solution

The present disclosure provides a chitinolytic enzyme derived from *Clostridium cellulovorans*, which includes an amino acid sequence of SEQ ID NO: 1.

In addition, the present disclosure provides a chitinolytic enzyme derived from *Clostridium cellulovorans*, which is encoded by a base sequence of SEQ ID NO: 2.

In an exemplary embodiment of the present disclosure, the enzyme may have binding ability and degrading ability for chitin.

In another exemplary embodiment of the present disclosure, the enzyme may degrade the terminal of chitin.

In addition, the present disclosure provides a method for preparing a chitinolytic enzyme, which includes: (1) a step of preparing a recombinant expression vector including a base sequence of SEO ID NO: 2; (2) a step of preparing a transformant by introducing the recombinant expression vector into a host cell; (3) a step of culturing the transformant; and (4) a step of lysing and centrifuging the transformant and obtaining a supernatant thereof.

In an exemplary embodiment of the present disclosure, the vector may be a pColdII plasmid vector.

In another exemplary embodiment of the present disclosure, the host cell may be *E. coli* (*Escherichia coli*).

In another exemplary embodiment of the present disclosure, a pTf16 chaperone vector may be further introduced into the transformant.

In addition, the present disclosure provides an antifungal composition containing the chitinolytic enzyme as an active ingredient.

In an exemplary embodiment of the present disclosure, the fungus may be one or more selected from a group consisting of *Trametes versicolor, Fomitopsis palustris* and *Gloeophyllum trabeum*.

In another exemplary embodiment of the present disclosure, the antifungal composition may be an anti-mold composition.

Advantageous Effects

The present disclosure has identified the chitin degrading and binding ability of exo-β-N-acetylglucosaminidase encoded by the Clocel_3193 gene of *Clostridium cellulo-* vorans and provides the same as a chitinolytic enzyme for producing lignocellulosic biomass. The present disclosure enables use of chitin biomass, N-acetylglucosamine which has not been easily used as a raw material and enables environment-friendly production of N-acetylglucosamine. In addition, the Clocel_3193 may be used as an antifungal agent which inhibits the proliferation and growth of fungi whose cell wall is mainly composed of chitin due to its chitin degrading and binding ability.

BRIEF DESCRIPTION OF DRAWINGS

FIG. 1 shows the function of the exo-β-N-acetylglucosaminidase (Clocel_3193) gene predicted from its sequence.

FIG. 2 schematically shows a recombinant vector pColdII::Clocel_3193 and a pTf16 chaperon vector in which the Clocel_3193 gene is inserted.

FIG. 3 shows a result of expressing Clocel_3193 in BL21(DE3)_Clocel_3193 which is a transformant in which pColdII::Clocel_3193 is introduced.

FIG. 4 shows a result of investigating the binding ability of Clocel_3193 to an insoluble substrate associated with lignocellulosic biomass.

FIG. 5 shows a result of investigating the degrading ability of Clocel_3193.

FIG. 6 shows a result of investigating the binding ability of Clocel_3193 to molds.

FIG. 7 shows a result of investigating the production of N-acetylglucosamine through degradation of molds by Clocel_3193.

BEST MODE FOR CARRYING OUT INVENTION

The inventors of the present disclosure have identified, through sequence analysis of the Clocel_3193 gene (Gene ID: 9610087) of *Clostridium cellulovorans*, the function of which has not been elucidated yet, that a protein encoded by the gene is exo-β-N-acetylglucosaminidase, have identified the selective binding and degrading ability of the Clocel_3193 for chitin, and have completed.

Thus, the present disclosure provides a chitinolytic enzyme derived from *Clostridium cellulovorans*.

The chitinolytic enzyme may be an exo-β-N-acetylglucosaminidase including or consisting of an amino acid sequence of SEQ ID NO: 1, and the enzyme may be encoded by a base sequence of SEQ ID NO: 2.

Lignocellulosic biomass (agricultural byproducts such as wood, grass, straw, hull, etc.) is utilized as a biofuel from which energy such as methane, ethanol and hydrogen can be produced through thermal degradation and fermentation processes together with sugar biomass (sugarcane, sugar beet, etc.) and starch biomass (grains, potato, etc.). The chemical compositions and contents of the main components of lignocellulosic biomass are different depending on the kind, age, etc. of trees. In general, the lignocellulosic biomass is composed of cellulose (40-50%), hemicellulose (25-35%) and lignin (15-20%). Cellulose is a polymer compound composed of glucose units regularly linked by hydrogen bond and van der Waals force. Hemicellulose consists of pentoses such as xylose and arabinose linked by β-1,4 linkages and serves as an adhesive between cellulose and lignin. Lignin is an insoluble, hardly degradable polymer compound wherein aromatic compounds having phenylpropanoid units are linked irregularly and prevents degradation of polysaccharides.

In an exemplary embodiment of the present disclosure, as a result of reacting Clocel_3193 with Avicel and xylan, which are main substrates of *Clostridium cellulovorans*, and chitin as a substrate for predicting the function of Clocel_3193 and quantitatively analyzing the amount of the protein not bound to each substrate, it as confirmed that Clocel_3193 has superior selective binding ability to chitin. It is expected that the binding ability of Clocel_3193 is due to an unknown part. From the above result, it can be seen that the unique binding ability of Clocel_3193 to chitin, which is not directly related with general lignocellulosic biomass, is exerted by the unknown part.

Therefore, the chitinolytic enzyme of the present disclosure can degrade chitin-based substrates quickly due to the binding ability.

In another exemplary embodiment of the present disclosure, in consideration of the fact that the cell wall of fungi is composed of chitin, the binding and degrading ability of Clocel_3193 for molds was investigated. As a result, it was confirmed that Clocel_3193 degrades the cell wall of *Trametes versicolor*, *Fomitopsis palustris* and *Gloeophyllum trabeum* by binding thereto and produces N-acetylglucosamine as a degradation product.

Therefore, the chitinolytic enzyme of the present disclosure can be used as an antifungal composition, particularly an anti-mold composition.

The fungi to which the chitinolytic enzyme of the present disclosure can be applied as an antifungal composition are not limited as long as the main component of the cell wall is chitin.

In another exemplary embodiment of the present disclosure, it was confirmed that Clocel_3193 can be produced in large scale by inserting the Clocel_3193 gene with a gene encoding a signal peptide removed into a pColdII vector and transforming the vector into *E. coli*.

The present disclosure provides a method for preparing a chitinolytic enzyme, which includes:

(1) a step of preparing a recombinant expression vector including a base sequence of SEQ ID NO: 2;

(2) a step of preparing a transformant by introducing the recombinant expression vector into a host cell;

(3) a step of culturing the transformant; and (4) a step of lysing and centrifuging the transformant and obtaining a supernatant thereof.

Although a pColdII plasmid is used in an exemplary embodiment of the present disclosure as the "vector", any DNA construct including a DNA sequence operably linked to a suitable regulatory sequence capable of expressing DNA in a suitable host, without limitation. Accordingly, the vector may be a plasmid, a phage particle, or simply a potential genomic insert. Once transformed into a suitable host, the vector may replicate and function independently of the host genome, or relay in some cases be integrated into the genome itself. In the present disclosure, the terms "plasmid" and "vector" are sometimes used interchangeably, since the plasmid is the most commonly used form of vector and is used in an exemplary embodiment of the present disclosure. However, the present disclosure also includes other forms of vectors having the same function, which are known or are to be known in the art.

The "recombinant expression vector" of the present disclosure generally means a double-stranded DNA fragment which functions as a recombinant carrier into which a heterologous DNA fragment is inserted. Here, the heterologous DNA means a heterotype DNA, which is not naturally found in a host cell. The expression vector can self-replicate regardless of the chromosomal DNA of a host once introduced into the host cell, and can produce several copies of the vector and (heterologous) DNA inserted thereinto. Although E. coli is used as the host cell in an exemplary embodiment of the present disclosure, the host cell is not limited as long as the recombinant expression vector can be replicated and can express the target gene in the cell.

The vector may include a promoter operatively linked to the cloned gene. In the present disclosure, the "promoter" promotes the expression of the gene to be transfected, and the promoter may include not only basal elements necessary for transcription but also an enhancer that can be used for promotion and regulation of the expression. In an exemplary embodiment of the present disclosure, a pTf16 chaperone vector may be further introduced into the transformant to enhance the expression level of the target gene.

In the present disclosure, the "transformation" or "transfection" means introduction of a DNA into a host to be replicable as an extrachromosomal factor or for integration into the chromosome.

The present disclosure can be changed variously and may have various exemplary embodiments. Hereinafter, specific examples will be described in detail through drawings. However, the present disclosure is not limited to the specific examples and it should be understood that all changes, equivalents or substitutes within the technical scope of the present disclosure. In the present disclosure, a detailed description of well-known technologies will be omitted to avoid obscuring the subject matter of the present disclosure.

EXAMPLES

Example 1. Securing of Novel exo-β-N-acetylglucosaminidase Derived from *Clostridium cellulovorans* and Prediction of Function Through Sequence Analysis The location and sequence of the exo-β-N-acetylglucosaminidase gene (Clocel_3193, Gene ID: 9610087) were investigated from the entire genome of *Clostridium cellulovorans*. Sequence analysis was conducted based on Signal P and NCBI Blast databases. As a result, it was predicted that the gene consists of a signal peptide associated with external secretion of proteins (amino acids 1-21), an unknown sequence with 74.2% homology to a protein including the F5/8 type C domain known to have binding ability for N-acetylglucosamine (amino acids 22-469), a chitobiase/β-hexosaminidase C-terminal domain (amino acids 470-536) and a dockerin repeat necessary for connection to a cellulosome as an enzyme complex (amino acids 578-598) (see FIG. 1). The finally expressed part excluding the signal peptide which affects enzyme expression was amplified by PCR by preparing a forward primer in the 5' direction (restriction enzyme BamHI) and a reverse primer in the 3' direction (restriction enzyme EcoRI) from the genomic DNA. The primers are described in Table 1. Restriction enzyme recognition sequences are underlined. The restriction enzymes are BamHI and EcoRI.

TABLE 1

| Forward primer | 5'-ATA<u>GGATCC</u>AAAATAAATTTCACTGTAA-3' (SEQ ID NO: 3) |
|---|---|
| Reverse primer | 5'-CG<u>GAATTC</u>ACTAAGTAATTTTTTCTTTAAA-3' (SEQ ID NO: 4) |

Example 2. Cloning for Expression of exo-β-N-acetylglucosaminidase Gene in *E. coli* and Introduction into *E. coli*

After amplifying the exo-β-N-acetylglucosaminidase gene (Clocel_3193) obtained in Example 1 through PCR except for the signal peptide as an enzyme expression inhibiting element and ligating into a pColdII vector, which is one of *E. coli* expression vectors, with BamHI and EcoRI using a ligation kit, the vector was transformed into *E. coli* (*Escherichia coli*) BL21(DE3). In addition, a pTf16 chaperon vector was introduced together in order to increase the expression level of Clocel_3193 (see FIG. 2). The resultant recombinant vector was named pColdII::Clocel_3193, and the *E. coli* transformant was named BL21(DE3)_Clocel_3193.

Example 3. Expression of Recombinant Clocel_1319 in *E. coli* Transformant

For investigation of the expression of Clocel_3193 in the transformant, purification using a His-tag and SDS-PAGE were conducted. More specifically, the recombinant strain was inoculated into an LB medium containing ampicillin and then cultured in advance at 37° C. for 24 hours in order to induce protein expression. Then, after inoculating the preculture to 250 mL of an LB medium containing ampicillin, IPTG was added at a final concentration of 1 mM as an inducer for inducing the expression of Clocel_3193 when optical density at 600 nm (O.D.$_{600}$) was about 1.0. After culturing for about 18-20 hours, the cells were obtained through centrifugation. Then, the cells were lysed by sonication and then centrifuged. Then, the resulting supernatant was purified by affinity chromatography with a His-tag attached to the N-terminal of the protein using an imidazole gradient (~20 mM). As a result of conducting electrophoresis on a 10% SDS-PAGE gel and staining with a Coomassie Blue dye, the predicted protein (65 kDa) was observed at the corresponding location (see FIG. 3).

Example 4. Investigation of Binding Ability of Clocel_3193 to Representative Lignocellulosic Biomass and Insoluble Substrate Selected Through Functional Prediction In order to investigate the selective binding ability of the Clocel_3193 obtained in Example 3 for chitin, the Clocel_3193 was reacted with each of Avicel, xylan and chitin. 0.06 g of each substrate was prepared and the final concentration of albumin as a control group and the enzyme (Clocel_3193) as a test group was adjusted to about 100 μg/mL. 100 mM sodium phosphate (pH 7.0) was used as a binding ability assay buffer. After conducting reaction at 15° C. under stirring at 300 rpm for 45 minutes and centrifuging at 1,000 g for 1 minute, the quantity of proteins remaining in the supernatant was measured by the Bradford assay. After treating 10 μL of protein or enzyme with 400 μL of a Bradford reagent and mixing well, absorbance was measured at 595 nm using a spectrophotometer. Albumin was used as a reference protein for quantitative analysis of the protein and enzyme. As a result, Clocel_3193 was confirmed to have superior selective binding ability to chitin (see FIG. 4).

Example 5. Investigation of Degradation Pattern of Clocel_3193

Since Clocel_3193 has a C-terminal found in chitobiase and β-hexosaminidase, it is expected to have catalytic activity comparable to those of the enzymes. Therefore, in order to investigate whether the Clocel_3193 of the present disclosure has a degradation pattern similar to that of chitobiase and β-hexosaminidase, reaction was conducted with 1.5 mM 4-nitrophenyl N-acetyl-β-D-glucosaminide (pNPβG$_1$), 4-nitrophenyl-N,N-diacetyl-β-D-chitobioside (pNPβG$_2$) and 4-nitrophenyl-β-D-N,N,N-triacetylchitotriose (pNPβG$_3$). The reaction was conducted at 35° C. for 16-24 hours. The reaction was terminated by adding a 0.1 N NaOH solution of the same volume as the reaction solution. Then, the absorbance of the reaction solution was measured at 405 nm using a spectrophotometer. It was confirmed that Clocel_3193 has a degradation pattern of recognizing one sugar and producing N-acetylglucosamine by cleaving the same at the terminal (see FIG. 5).

Example 6. Investigation of Binding Ability of Clocel_3193 to Mold

The cell wall of molds is composed of chitin. In order to investigate the mold binding ability of the Clocel_3193 obtained in Example 3, *Trametes versicolor*, *Fomitopsis palustris* and *Gloeophyllum trabeum* were cultured in a PDB medium for 2 weeks and the hypha of the mold was collected through gauze. The hypha was washed 3 times with sterilized distilled water and then prepared into powder after removing moisture using a drying oven. 0.06 g of the prepared mold powder was treated with albumin as a control group or Clocel_3193 as a test group at a final concentration of about 100 μg/mL using 100 mM sodium phosphate (pH 8.0) as a buffer. After conducting reaction at 15° C. under stirring at 300 rpm for 45 minutes and centrifuging at 1,000 g for 1 minute, the quantity of proteins remaining in the supernatant was measured by the Bradford assay. After treating 10 μL of protein or enzyme with 400 μL of a Bradford reagent and mixing well, absorbance was measured at 595 nm using a spectrophotometer. Albumin was used as a reference protein for quantitative analysis of the protein and enzyme. As a result, Clocel_3193 was confirmed to have binding ability to mold (see FIG. 6).

Example 7. Investigation of Mold Degrading Ability of Clocel_3193

It was investigated whether Clocel_3193 bound to molds has mold degrading ability. Specifically, *Trametes versicolor*, *Fomitopsis palustris* and *Gloeophyllum trabeum* were cultured in a PDB medium for 2 weeks and the hypha of the mold was collected through gauze. The hypha was washed 3 times with sterilized distilled water and then prepared into powder after removing moisture using a drying oven. 0.41 g of the powder was prepared as a substrate. 0.41 g of the mold powder was added to 100 mM sodium phosphate (pH 6.0) as a buffer. Then, reaction was conducted at 35° C. and 200 rpm for 4 days. The concentration of the enzyme used was about 100 μg/mL. After the reaction, the reaction solution was centrifuged at 13,000 rpm for 10 minutes and the supernatant was filtered and analyzed by HPLC. A refractive index detector (RID) and an Aminex HPX-87H ion-exchange column (300 mm×7.8 mm) were used. 5 mM sulfuric acid was used as a mobile phase and the separated sugar was measured at a rate of 0.5 mL/min. The sample injection volume was 10 μL. As a result, it was confirmed that Clocel_3193 can produce N-acetylglucosamine by degrading mold (see FIG. 7).

While the exemplary embodiments have been shown and described, it will be understood by those skilled in the art that various changes in form and details may be made thereto without departing from the spirit and scope of this disclosure as defined by the appended claims.

The invention claimed is:

1. A method for producing N-actyl glucosamine, comprising:
   a step of mixing a chitinolytic enzyme comprising SEQ ID NO: 1 with chitin or biomass comprising chitin.

2. The method of claim 1, further comprising the following steps prior to the step of mixing:
   a step of preparing a base sequence comprising SEQ ID NO: 2;
   a step of preparing a recombinant expression vector comprising the base sequence comprising SEQ ID NO: 2;
   a step of preparing a transformant by introducing the recombinant expression vector into a host cell;
   a step of culturing the transformant; and
   a step of lysing and centrifuging the transformant and obtaining a supernatant thereof to prepare the chitinolytic enzyme comprising SEQ ID NO: 1.

3. The method according to claim 2, wherein the vector is a pColdII plasmid vector.

4. The method according to claim 2, wherein the host cell is *E. coli* (*Escherichia coli*).

5. The method according to claim 2, wherein a pTf16 chaperone vector is further introduced into the transformant.

* * * * *

SEQUENCE LISTING

```
<160> NUMBER OF SEQ ID NOS: 4

<210> SEQ ID NO 1
<211> LENGTH: 568
<212> TYPE: PRT
<213> ORGANISM: Clostridium cellulovorans_Clocel_3193

<400> SEQUENCE: 1

Lys Ile Asn Phe Thr Val Ser Tyr Thr Ser Ala Val Gly Lys Thr Glu
1               5                   10                  15

Asn Tyr Thr Cys Ala Thr Arg Asp Ser Phe Tyr Asp Leu Asn Asp Asn
                20                  25                  30

Ser Val Asn Arg Ala Thr Ser Glu His Phe Gln Ile Ile Trp Gly Asn
            35                  40                  45

Gly Asp Thr Thr Gly Thr Val Asn Gln Glu Leu Val Lys Gly Asn Leu
        50                  55                  60

Gln Asn Leu Glu Ala Ile Arg Asp Phe Tyr Val Asn Val Met Gly Phe
65                  70                  75                  80

Val Asp Thr Ser Val Ser Val Asn Ser Pro Leu Thr Ser Ser Asn His
                85                  90                  95

Tyr Lys Thr Asn Val Tyr Ile Ser Asn Thr Gly Leu Ser Lys Ile Thr
            100                 105                 110

Asp Asp Trp Ala Tyr Met Ser Ser Asp Gly Glu Gly Phe Ala Phe Leu
        115                 120                 125
```

-continued

Val Leu His Pro Gly Ala Met Arg Val Asp Pro Pro Ser Trp Val Val
    130                 135                 140

Pro His Glu Tyr Ala His Ala Ile Thr Met His Gln Arg Gly Val Ile
145                 150                 155                 160

Asp Ala Pro Trp Tyr Glu Val Thr Ala Asn Trp Phe Arg Asp Gln Tyr
                165                 170                 175

Leu Gly Ser Ser Phe Tyr Lys Tyr Gly Asn Asn Val Tyr Gly Pro Asp
            180                 185                 190

Ser Asp Phe Phe Arg Pro Ile Val Leu Asn Ser Asp Tyr Tyr Phe Pro
        195                 200                 205

His Leu Lys Asn Tyr Tyr Asp Ala Trp Pro Phe Leu Leu Tyr Val Thr
    210                 215                 220

Glu Asn Pro Asp Gln Met Lys Gly Leu Gly Leu Glu Val Met Lys Ala
225                 230                 235                 240

Met Phe Lys Asp Thr Asn Asn Glu Val Met Phe Lys Lys Leu Glu Arg
                245                 250                 255

Leu Ser Gly Thr Ser Ala Lys Asp Met Leu Gly Gly Tyr Ala Arg Arg
            260                 265                 270

Met Val Thr Phe Asp Phe Lys Arg Gln Ala Asn Tyr Lys Lys Tyr Tyr
        275                 280                 285

Asp Glu Leu Ile Ala Glu Asp Ser Ala Asn Tyr Asn Lys Ile Tyr Thr
    290                 295                 300

Thr Leu Glu Asn Asp Ser Asn Gly Trp Phe Lys Val Pro Ser Ser Arg
305                 310                 315                 320

Ala Pro Gln Gln Gly Gly Tyr Asn Ile Ile Pro Leu Asn Ile Asp Leu
                325                 330                 335

Lys Ser Lys Gln Val Val Asn Phe Gln Gly Asn Ser Ser Glu Val
            340                 345                 350

Gly Ala Asp Trp Arg Ala Ser Ile Val Ala Lys Thr Lys Thr Gly Gln
        355                 360                 365

Thr Arg Tyr Ser Thr Met Trp Asn Ser Gly Thr Asn Thr Leu Asn Leu
    370                 375                 380

Gln Gly Asp Glu Glu Lys Val Tyr Leu Val Val Cys Ala Thr Pro Lys
385                 390                 395                 400

Glu Met Leu Asn Leu Thr Ser Phe Asp Leu Asp Val Val Gly Thr Arg
                405                 410                 415

Tyr Pro Tyr Lys Val Gln Ile Ser Thr Asn Ser Ala Val Ser Lys Val
            420                 425                 430

Glu Met Pro Thr Val Ser Val Ala Ala Gly Ser Tyr Asn Ala Ala Gln
        435                 440                 445

Thr Ile Ser Leu Ser Ser Lys Thr Ser Gly Thr Thr Ile Tyr Tyr Thr
    450                 455                 460

Leu Asp Gly Ser Thr Pro Thr Ala Ser Ser Thr Ala Tyr Ser Ser Pro
465                 470                 475                 480

Ile Val Val Ser Lys Asn Thr Thr Ile Lys Ala Val Ala Ile Lys Ser
                485                 490                 495

Gly Met Thr Asn Ser Asp Ile Thr Ser Ala Thr Tyr Thr Ile Ser Ile
            500                 505                 510

Ile Gly Asp Val Asn Glu Asp Gly Arg Val Asn Ala Ile Asp Tyr Ala
        515                 520                 525

Asn Ile Lys Ser Tyr Leu Leu Ala Asn Ser Thr Lys Ile Asn Leu Lys
    530                 535                 540

Asn Ala Asp Met Asn Asn Asp Ser Lys Val Asn Ala Ile Asp Leu Ala 545              550              555              560

Leu Leu Lys Lys Lys Leu Leu Ser
                565

<210> SEQ ID NO 2
<211> LENGTH: 1707
<212> TYPE: DNA
<213> ORGANISM: Clostridium cellulovorans_Clocel_3193

<400> SEQUENCE: 2

| | | | | | |
|---|---|---|---|---|---|
| aaaataaatt | tcactgtaag | ttatacttca | gcagtgggaa | agactgaaaa | ttatacttgt | 60 |
| gcaacaagag | attcctttta | tgatttgaat | gataattcag | ttaacagagc | tacttcagaa | 120 |
| catttccaaa | taatttgggg | aaatggtgat | actacaggaa | ctgttaatca | agaattagta | 180 |
| aaaggtaatt | tacaaaacct | agaggcaata | agagatttct | atgttaatgt | aatgggcttt | 240 |
| gtagatacta | gtgtatctgt | taatagtcca | ctaactagca | gcaatcacta | caaaacaaat | 300 |
| gtgtacatat | ccaatactgg | actttcaaag | attacagatg | attgggcata | tatgtcttct | 360 |
| gacggagaag | gctttgctttt | cttagttta | catccaggag | ctatgcgtgt | tgacccacca | 420 |
| agttgggtag | ttcctcacga | atatgctcat | gccattacta | tgcatcaacg | tggtgttatc | 480 |
| gatgctcctt | ggtatgaagt | aacagcaaat | tggttcagag | atcaatattt | aggaagtagt | 540 |
| ttttataagt | atggaaataa | tgtttatgga | cctgattcag | acttctttag | gccaatagtc | 600 |
| ttgaactcag | actactactt | tccacatttg | aagaactatt | atgatgcttg | gccattctta | 660 |
| ctatatgtaa | ctgaaaatcc | tgaccaaatg | aaaggattag | gtcttgaagt | aatgaaagcg | 720 |
| atgtttaagg | acactaataa | tgaagttatg | tttaagaaat | tagagagatt | atctggaaca | 780 |
| tctgctaaag | atatgttagg | tggctatgct | agaagaatgg | taacctttga | ttttaagaga | 840 |
| caagctaatt | ataaaaaata | ttatgatgaa | ttaatagcag | aggacagtgc | aaattataat | 900 |
| aaaatttata | caaccttaga | aaatgatagt | aatggatggt | ttaaggttcc | tagctcaagg | 960 |
| gctccacaac | aaggtggata | taatattatt | ccacttaaca | tagatctaaa | gagtaagcag | 1020 |
| gtagtcgtta | attttcaagg | aaatagttca | gaagtagggg | cagattggcg | tgcaagcatt | 1080 |
| gttgctaaaa | caaaaactgg | acaaactaga | tattctacaa | tgtggaatag | tggaactaac | 1140 |
| actttgaatc | tacaaggaga | tgaagaaaaa | gtttatcttg | tagtatgtgc | aactccgaag | 1200 |
| gaaatgctta | atttaacttc | atttgattta | gatgtagtag | gaacaagata | tccatataaa | 1260 |
| gtgcaaatat | caacgaatag | cgctgtttca | aaggtagaaa | tgccaactgt | tagtgtagca | 1320 |
| gcaggtagtt | acaatgctgc | acaaacaata | tcacttagca | gtaaaacttc | aggtacaact | 1380 |
| atatattata | cacttgacgg | aagtactcca | acagcttcat | ctactgccta | tagtagtccg | 1440 |
| atagtagtat | caaaaaatac | aactattaag | gctgttgcaa | taaagagtgg | aatgacaaac | 1500 |
| tctgatataa | cttctgctac | atatacaatt | tctataattg | gtgatgttaa | tgaagatggt | 1560 |
| cgtgtaaatg | caattgatta | tgccaatatt | aagagctatt | tactggctaa | ttcaacaaag | 1620 |
| ataaatttaa | agaacgcaga | tatgaataat | gatagtaaag | taaatgccat | cgatttagca | 1680 |
| cttttaaaga | aaaaattact | tagttaa | | | | 1707 |

<210> SEQ ID NO 3
<211> LENGTH: 28
<212> TYPE: DNA
<213> ORGANISM: Artificial Sequence
<220> FEATURE:
<223> OTHER INFORMATION: Forward primer

```
<400> SEQUENCE: 3
ataggatcca aaataaattt cactgtaa                                              28

<210> SEQ ID NO 4
<211> LENGTH: 30
<212> TYPE: DNA
<213> ORGANISM: Artificial Sequence
<220> FEATURE:
<223> OTHER INFORMATION: Reverse primer

<400> SEQUENCE: 4
cggaattcac taagtaattt tttctttaaa                                            30
```